(12) United States Patent
Yuen et al.

(10) Patent No.: US 11,091,427 B2
(45) Date of Patent: Aug. 17, 2021

(54) BUILDING BLOCKS FOR STAPLED PEPTIDES

(71) Applicant: Agency for Science, Technology and Research, Singapore (SG)

(72) Inventors: Tsz Ying Yuen, Singapore (SG); Charles William Johannes, Singapore (SG); Greg Verdine, Cambridge, MA (US)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 16/497,299

(22) PCT Filed: Mar. 23, 2018

(86) PCT No.: PCT/SG2018/050129
§ 371 (c)(1),
(2) Date: Sep. 24, 2019

(87) PCT Pub. No.: WO2018/174826
PCT Pub. Date: Sep. 27, 2018

(65) Prior Publication Data
US 2020/0031760 A1 Jan. 30, 2020

(30) Foreign Application Priority Data
Mar. 24, 2017 (SG) .............................. 10201702443S

(51) Int. Cl.
| | | |
|---|---|---|
| C07C 227/12 | (2006.01) | |
| C07C 229/48 | (2006.01) | |
| C07D 265/32 | (2006.01) | |
| C07D 265/34 | (2006.01) | |
| C07K 5/08 | (2006.01) | |
| C07K 7/06 | (2006.01) | |

(52) U.S. Cl.
CPC .......... *C07C 227/12* (2013.01); *C07C 229/48* (2013.01); *C07D 265/32* (2013.01); *C07D 265/34* (2013.01); *C07K 5/0802* (2013.01); *C07K 7/06* (2013.01); *C07C 2601/02* (2017.05)

(58) Field of Classification Search
CPC .............................. C07C 227/12; C07D 265/32
USPC ......................................................... 544/71
See application file for complete search history.

(56) References Cited

U.S. PATENT DOCUMENTS
2016/0185821 A1 6/2016 Mangold et al.

FOREIGN PATENT DOCUMENTS
| WO | 0059929 | 10/2000 |
| WO | 2008/121767 | 10/2008 |

OTHER PUBLICATIONS

Hilinski et al. "Stitchedf alpha-Helical Peptides via Bis Ring-Closing Materials", J. Am. Chem. Soc. 136(35):12314-12322 (2014).
International Preliminary Report on Patentability corresponding to International Patent Application No. PCT/SG2018/050135 dated Oct. 3, 2019.
International Search Report and the Written Opinion of the International Searching Authority corresponding to International Patent Application No. PCT/SG2018/050135 dated Jun. 4, 2018.
Kim et al. "Synthesis of all-hydrocarbon stapled alpha-helical peptides by ring-closing olefin metathesis", Nature Protocols 6(6):761-771 (2011).
Mangold et al. "Stereoselective synthesis of macrocyclic peptides via a dual olefin metathesis and ethenolysis approach", Chem. Sci. 6(8):4561-4569 (2015).
Mangold et al. "Z-Selective Olefin Metathesis on Peptides: Investigation of Side-Chain Influence, Preorganization, and Guidelines in Substrate Selection", J. Am. Chem. Soc. 136(35):12469-12478 (2014).
Sanchez-Murcia et al. "Comparison of hydrocarbon-and lactam-bridged cyclic peptides as dimerization inhibitors of Leishmania infantum trypanothione reductase", RSC Adv. 69(5):55784-55794 (2015).
Zhang et al. "Influence of alpha-methylation in constructing stapled peptides with olefin metathesis", Tetrahedron 70(42):7621-7626 (2014).

(Continued)

*Primary Examiner* — Kahsay Habte
(74) *Attorney, Agent, or Firm* — Myers Bigel, P.A.

(57) ABSTRACT

This invention relates to a method for producing an alkenyl 1-aminocyclopropane-1-carboxylic acid of Formula I wherein $R^1$ is a protecting group, n is an integer between 1 and 10, and A and B are chiral centres such that when A is S, B is R and when A is R, B is S. The method comprises a stereoselective formation of the cyclopropane moiety by cycloaddition onto a double bond, in a molecule comprising a chiral template, Formula Ic. Further provided is the use of Formula I in the production of stapled peptides.

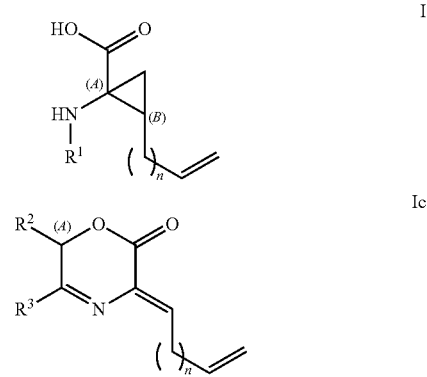

19 Claims, 1 Drawing Sheet

(56) References Cited

OTHER PUBLICATIONS

Abellan et al. "New Oxazinone and Pyrazinone Derivatives as Chiral Reagents for the Asymmetric Synthesis of alpha-Amino Acids" Journal of Heterocyclic Chemistry, 37(3):467-479 (2009).
International Preliminary Report on Patentability corresponding to International Patent Application No. PCT/SG2018/050129 (7 pages) (dated Sep. 24, 2019).
International Search Report and the Written Opinion of the International Searching Authority corresponding to International Patent Application No. PCT/SG2018/050129 (11 pages) (dated Jun. 7, 2018).
Tan et al. "Stapled peptide design: principles and roles of computation" Drug Discovery Today, 21(10):1642-1653 (2016).

BUILDING BLOCKS FOR STAPLED PEPTIDES

FIELD

This invention relates to the synthesis of stapled peptide building blocks.

BACKGROUND

Stapled peptides incorporate an all-hydrocarbon linker that can reinforce the secondary structure of short peptides. Since their inception in 2000, 2 candidates (ALRN-5281 and ALRN-6924) have successfully entered phase I clinical trial and others have demonstrated promising therapeutic potential. These candidate peptides introduced rigidifying elements with the aim of increasing the extent of α-helix stabilisation and protease resistance. One example of a rigidifying element is a cyclopropyl ring from which the hydrocarbon bridge is attached. Structurally, these alkenyl 1-aminocyclopropane-1-carboxylic acid ('ACC') building blocks were designed based on existing "rules" governing the linker of peptidic side chains (FIG. 1).

The use of long-chain alkenyl ACCs as stapled peptide building blocks remains unexplored. However, several potent HCV NS3/4a protease inhibitors have the related vinyl-substituted ACC2 incorporated into the backbone as a common motif (FIG. 2).

The synthesis of vinyl ACCs via a SN2-SN2' dialkylation of di-tert-butyl malonate has been described previously which results in a racemic mixture being produced.

Currently, in order to isolate a specific stereoisomer of ACCs, the racemic mixture of compounds is further transformed. For example a separation protocol for vinyl-ACCs using Alcalase 2.4 L, an enzyme that selectively hydrolysed esters with the (S)-configuration, was developed as a method of obtaining a single stereoisomer of the stapled peptide (Scheme 1). Upon complete consumption of the (S)-isomer, the carboxylic acid was siphoned off and the remaining (R)-ester was hydrolysed, resulting in the desired (1R,2S)-ACC.

Scheme 1
Scheme 1. Enzymatic resolution of racemic ACCs.

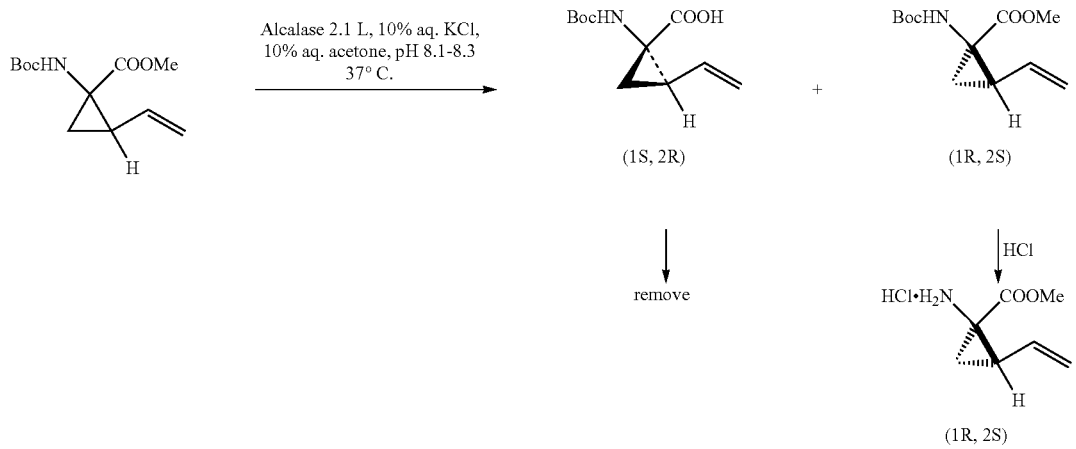

The only known asymmetric approach to (1S,2R)-ACCs involved the use of chiral glycine templates to direct enantioselectivity during the cyclopropanation step. The glycine templates can be conveniently assembled from amino acid type derivatives (Scheme 2). The substituent on C-6 acts to block one face of the heterocycle so that ensuing cyclopropanation becomes stereoselective. However, the synthesis of (1R,2S)-ACCs using this approach has not been demonstrated.

Scheme 2
Scheme 2. Reagents and conditions: (i) RCHO, TBAB, $K_2CO_3$, MeCN, r.t.; (ii) $Me_3SOI$, NaH, DMF, r.t.; (iii) HCl, 150° C.

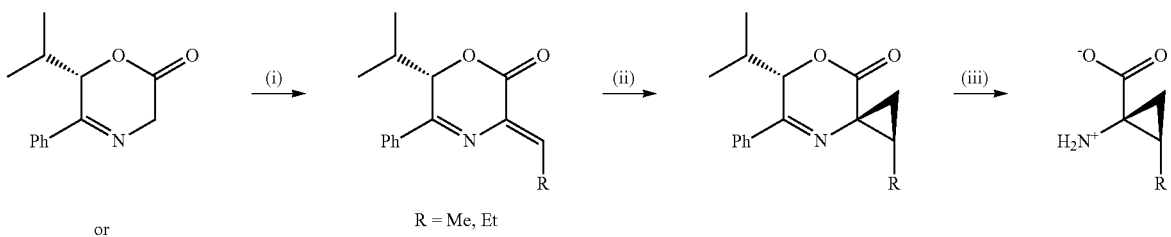

 (i)-(iii)

Hence, as stereoselective ACCs cannot be specifically made, the use of ACCs as building blocks in peptide synthesis is largely unexplored. The most established ACC synthesis methods are racemic in nature and require additional steps to isolate a specific stereoisomer, resulting in loss of about half of the product produced. Therefore, racemic approaches to these novel stapled peptide building blocks have limited appeal.

The class of alkenyl ACCs is novel and little structural information is available in the literature. Additionally, there is a lack of a stereoselective method for the production of ACCs whereby the requisite (1R,2S) or (1S,2R) stereocentres can be selected, as all current methods rely on the production of a racemic mixture which is then separated into the corresponding racemates. The asymmetric synthesis described herein allows the formation of either (1R,2S) or (1S,2R)-ACCs by simply changing the stereochemistry of the starting material.

The invention disclosed herein represents the first example of an asymmetric synthesis of long-chain alkenyl ACCs. Functionalisation of glycine templates with alkenyl aldehydes is also novel.

SUMMARY OF INVENTION

In a first aspect of the present invention, there is provided a method for producing a compound of Formula I

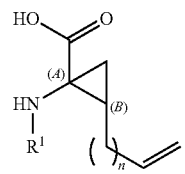
I wherein:
$R^1$ is a protecting group;
n is an integer between 1 and 10, and;
A and B are chiral centers such that when A is S, B is R and when A is R, B is S;
said method comprising the steps of:
a) condensing a chiral compound of Formula Ia

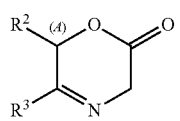
Ia with a compound of Formula Ib

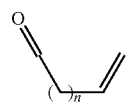
Ib to produce a compound of Formula Ic

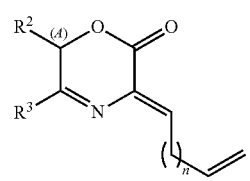
Ic wherein A is a chiral center, $R^2$ is an aliphatic group with a secondary or tertiary carbon atom covalently bonded to the chiral center A, and $R^3$ is aryl or heteroaryl;
b) reacting the non-terminal carbon-carbon double bond formed in step a) to produce a cyclopropyl group, so as to form a compound of Formula Id

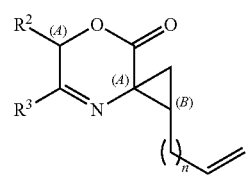
Id b. and;
c) hydrolyzing the compound of Formula Id and protecting an ensuing amine (i.e., a free amine produced by the hydrolysis) with an $R^1$ protecting group to produce the compound of Formula I.

The following options may be used in conjunction with the first aspect, either individually or in any suitable combination.

The $R^1$ group may be removable in basic solution. For example it may be Fmoc (fluorenylmethyloxycarbonyl), or it may be 9-(2-sulfo)fluorenylmethyl carbamate, or it may be Peoc (2-phosphonioethoxycarbonyl), or it may be Ppoc (1-Methyl-1-(triphenylphosphonio) ethyl). The $R^2$ group may be a branched hydrocarbyl group. It may be isopropyl, sec-butyl, tert-butyl or sec-pentyl. The $R^3$ group may be heteroaryl or it may be aryl. When $R^3$ is aryl, it may be phenyl. The variable n may be an integer between 1 and 10, or between 1 and 6, 1 and 4, 2 and 6, 2 and 4, 3 and 6 or 4 and 6. It may be any one of 1, 2, 3, 4, 5, 6, 7, 8, 9 or 10.

In the compound of Formula I, A may be S so that B is R, or A may be R so that B is S.

Step (a) may be conducted in the presence of a catalyst. It may be conducted in the presence of a base. It may be conducted in the presence of both a catalyst and a base. When a catalyst is used, the catalyst may be a tetraalkylammonium salt. The tetraalkylammonium salt may be tetra-n-butylammonium bromide or may be some other tetra-n-butylammonium halide. When a base is used, it may be a basic inorganic salt. It may be potassium carbonate. The condensation reaction of step (a) is conducted in a solvent. The solvent may be an aprotic solvent. It may be a polar solvent. It may be dichloromethane or it may be acetonitrile. The temperature at which step (a) is conducted may be between about 0° C. and about 25° C., e.g., between about 10° C. and 25° C., 15° C. and 25° C. or 20° C. and 25° C. It may be about 5, 10, 15, 20, or 25° C.

Step (b) may comprise the reaction of a compound of Formula Ic with a trialkyl sulfoxonium halide. The trialkyl sulfoxonium halide comprises three alkyl groups, each independently selected from methyl, ethyl, propyl, butyl and pentyl. At least one of the three alkyl groups should be methyl. The trialkyl sulfoxonium halide may comprise three methyl groups (i.e., it may be a trimethyl sulfoxonium halide). The halide of the trialkyl sulfoxonium halide may be fluoride, chloride, bromide, or iodide. The trialkyl sulfoxonium halide may be for example trimethyl sulfoxonium chloride. The reaction may be conducted in the presence of a group I hydride, e.g., it may be LiH, NaH, or KH. The reaction may be conducted in an organic solvent. The solvent may be a polar aprotic solvent. It may be tetrahydrofuran. The temperature at which step (b) is conducted may be between about 20° C. and 100° C., e.g., between about 20° C. and 50° C. or between 50° C. and 100° C. It may be for example about 20, 30, 40, 50, 60, 70, 80, 90 or 100° C.

Step (c) may use an aqueous strong base in conjunction with a salt of a protecting group. The aqueous strong base may be LiOH, NaOH, KOH or NH$_4$OH. The protecting group precursor salt may be a halide salt of general formula R$^1$X, wherein R$^1$ may be a protecting group removable in a basic solution and X is a halide salt. The protecting group may be Fmoc(fluorenylmethyloxycarbonyl chloride), or it may be 9-(2-sulfo)fluorenylmethyl carbamate, or it may be Peoc (2-phosphonioethoxycarbonyl), or it may be Ppoc (1-Methyl-1-(triphenylphosphonio) ethyl). The halide salt may be fluoride, chloride, bromide or iodide. The salt of the protecting group may be Fmoc-Cl. The temperature at which step (c) is conducted may be between about 15° C. and 30° C., e.g., between about 15° C. and 25° C. or between 20° C. and 25° C. It may be for example 15, 20, 25 or 30° C. It may be room temperature.

The method may further comprise the step of preparing the compound of Formula Ia. In this step, the compound of Formula IIa

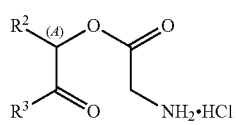

is dehydrated to form a compound of Formula Ia. The R$^2$ group may be a branched hydrocarbyl group, for example it may be isopropyl, sec-butyl, tert-butyl or sec-pentyl. The R$^3$ group may be heteroaryl or it may be aryl. When R$^3$ is aryl, it may be phenyl. The compound of Formula Ia may be formed in an acidified organic solvent. The organic solvent may be an organic ester, for example it may be ethyl acetate. The organic solvent may be acidified by a mineral acid. For example, the mineral acid may be HF, HCl, HBr, or HI. The mineral acid may be added to the organic solvent whilst in the gaseous state. The acidified organic solvent may be ethyl acetate acidified with gaseous HCl. The temperature at which the compound of Formula Ia is formed may be at a temperature between about 15° C. and about 30° C., e.g., between about 15° C. and 25° C. or between 20° C. and 25° C. It may be for example 15, 20, 25 or 30° C. It may be conducted at a room temperature. The dehydration reaction of this step may use a trialkylamine. The trialkylamine is added in an equimolar amount compared to the amount of the compound of Formula IIa present. The trialkylamine comprises three alkyl groups, each independently selected from the group comprising methyl, ethyl, propyl and butyl, for example the trialkylamine may be trimethylamine or it may be triethylamine. The temperature at which the dehydration reaction occurs may be between about 15° C. and 30° C., e.g., between about 15° C. and 25° C. or between 20° C. and 25° C. It may be for example 15, 20, 25 or 30° C. It may be conducted at a room temperature.

The method may further comprise the step of preparing a compound of Formula IIa by the adding of a glycine moiety to a compound of Formula IIb

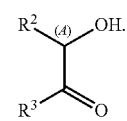

This addition reaction may comprise exposing a compound of Formula IIa to a nucleophilic catalyst, a coupling agent and a protected glycine. The nucleophilic catalyst may be a basic nucleophilic catalyst, for example it may be 4-dimethylaminopyridine. The coupling agent is capable of converting carboxylic acids to activated esters, for example it may be N,N'-dicyclohexylcarbodiimide, N,N'-diisopropylcarbodiimide or 1-ethyl-3-(3-dimethylaminopropyl)carbodiimide. The protected glycine has a protecting group bound to the glycine. The protecting group is an acid labile protectant group, for example it may be Boc (tert-butyloxycarbonyl), Adoc (adamantyloxycarbonyl), t-Bumeoc (1-(3, 5-di-t-butylphenyl)-1-methylethoxycarbonyl) or Adpoc (1-(1-Adamantyl)-1-methylethoxycarbonyl). The temperature at which this addition reaction occurs may be between about 15° C. and about 30° C., e.g., between about 15° C. and 25° C. or between 20° C. and 25° C. It may be for example 15, 20, 25 or 30° C. It may be conducted at room temperature.

The method may further comprise a step of preparing the compound of Formula IIb by exposing a compound of Formula IIc

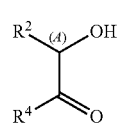

to a Grignard reagent of general formula R³MgBr in an organic dipolar aprotic solvent. The R² group may be a branched hydrocarbyl group, for example it may be isopropyl, sec-butyl, tert-butyl or sec-pentyl. The R³ group may be heteroaryl or it may be aryl. When R³ is aryl, it may be phenyl. The R⁴ group may be a dialkylamino group. The dialkylamino group consists of two alkyl groups, each alkyl group may be independently selected from the group comprising methyl, ethyl, propyl and butyl. The dialkylamino group may be a dimethylamino group. The Grignard reagent R³MgBr may be arylmagensium bromide. It may be phenylmagnesium bromide. The dipolar aprotic solvent may be THF. The temperature at which this reaction occurs may be between about −80° C. and about 25° C., e.g., between about −60° C. and about 25° C., or between −40° C. and 25° C., −20° C. and 25° C., 0° C. and 25° C., 10° C. and 20° C., 15° C. and 25° C. or 20° C. and 25° C. It may be for example −80, −75, −70, −65, −60, −55, −50, −45, −40, −35, −30, −25, —20, −15, −10, −5, 0, 5, 10, 15, 20 or 25° C. It may be conducted at a room temperature.

The method may further comprise a step of preparing a compound of Formula IIc by conducting an amidation reaction. In this amidation reaction, a compound of Formula IId

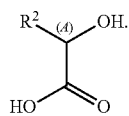

IId is exposed to a base, a catalyst, a dehydrating agent and a dialkylamine hydrohalide salt in a dipolar aprotic solvent. The dialkyamine hydrohalide salt is of a general formula R⁴H.HX. The R⁴ group may be a dialkylamino group. The dialkylamino group consists of two alkyl groups, each alkyl group is independently selected from the group comprising methyl, ethyl, propyl and butyl. It may be dimethylamino. X is a halogen. X may be fluorine, chlorine, bromine or iodine. The dialkyamine hydrohalide salt may be dimethylamine hydrochloride. The dehydrating agent may be N,N-dicyclohexylcarboiimide, or it may be (2-(thiophen-2-yl)phenyl)boronic acid. The catalyst may be hydroxybenzotriazole. The base may be a sterically-hindered base, such that it can only bind to protons. It may be N,N-diisopropylethylamine. The dipolar aprotic solvent may be THF. The temperature at which this reaction is conducted may be between about 15° C. and about 30° C., e.g., between about 15° C. and 25° C. or between 20° C. and 25° C. It may be for example 15, 20, 25 or 30° C. It may be conducted at a room temperature.

In one embodiment, the process of the present invention involves producing a compound of Formula I

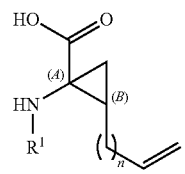

I wherein R¹ is a protecting group; n is 2, A is either S or R, and B is R when A is S or B is S when A is R. The process involves exposing a compound of Formula IId,

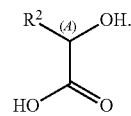

IId where R² is isopropyl, to N,N-diisopropylethylamine, hydroxybenzotriazole, N,N-dicyclohexylcarboiimide and dimethylamine hydrohalide in a dipolar aprotic solvent at a room temperature between about 15° C. and about 30° C., to produce a compound of Formula IIc. The next step in this process involves exposing the compound of Formula IIc

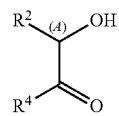

IIc where R² is isopropyl and R⁴ is N(Me)₂, to a Grignard reagent of formula R³MgBr in a dipolar aprotic solvent to produce a compound of Formula IIb. This may be conducted at an initial temperature of about −80° C. and allowing the temperature to rise to about 25° C. during the reaction. The compound of Formula IIb

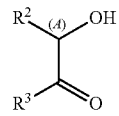

IIb where R² is isopropyl and R³ is aryl, is then exposed to 4-dimethylaminopyridine, N,N'-dicyclohexylcarbodiimide and a glycine that is amine-protected by a protecting group, at a temperature between about 15° C. and about 30° C., to produce a compound of Formula IIa. The next step is to expose a compound of Formula IIa

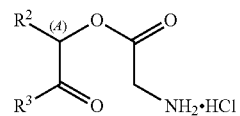

IIa where R² is isopropyl and R³ is aryl, to acidified ethyl acetate and a trialkylamine such as triethylamine at a temperature between about 15° C. and 30° C., to produce a compound of Formula Ia. The compound of Formula Ia

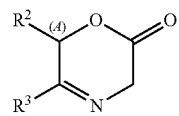

Ia where R² is isopropyl, R³ is aryl and A is either S or R, is then exposed to 4-pentenal, tetra-n-butylammonium bromide and potassium carbonate in acetonitrile or dichloromethane at a temperature between about 0° C. and about 25° C., to produce a compound of Formula Ic. The compound of Formula Ic

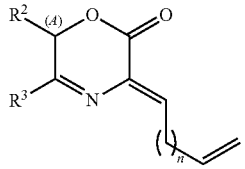

Ic where $R^2$ is isopropyl, $R^3$ is aryl, A is either S or R, and n is 2, is then exposed to trimethyl sulfoxonium chloride and a group I hydride in a dipolar aprotic solvent at a temperature between about 20° C. and about 100° C. to produce a compound of Formula Id. The next step is to expose a compound of Formula Id

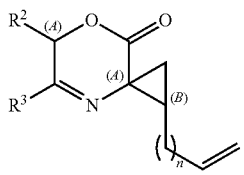

Id where $R^2$ is isopropyl, $R^3$ is aryl, A is either S or R, B is R when A is S or B is S when A is R, and n is 2, to aqueous NaOH in ethanol to hydrolyze the oxazine ring, and then expose this product to a halide salt of a protecting group in aqueous THF to protect the amine group, to produce a compound of Formula I

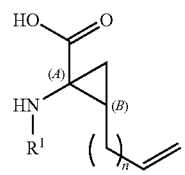

I where $R^1$ is a protecting group, A is S and B is R, or A is R and B is S, and n is 2.

In another embodiment, the process of the present invention involves producing a compound of Formula I

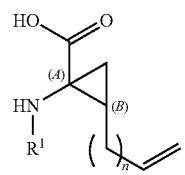

I wherein $R^1$ is a protecting group; n is 5, A is either S or R, B is R when A is S or B is S when A is R. The process involves exposing a compound of Formula IId,

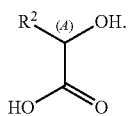

IId where $R^2$ is isopropyl, to N,N-diisopropylethylamine, hydroxybenzotriazole, N,N-dicyclohexylcarboiimide and dimethylamine hydrochloride in a dipolar aprotic solvent at a temperature between about 15° C. and about 30° C., to produce a compound of Formula IIc. The next step in this process involves exposing the compound of Formula IIc

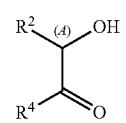

IIc where $R^2$ is isopropyl and $R^4$ is $N(Me)_2$, to a Grignard reagent of formula $R^3MgBr$ in THF to produce a compound of Formula IIb. This may be conducted at an initial temperature of about −80° C. and allowing the temperature to rise to about 25° C. during the reaction, The compound of Formula IIb

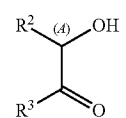

IIb where $R^2$ is isopropyl and $R^3$ is aryl, is then exposed to 4-dimethylaminopyridine, N,N'-dicyclohexylcarbodiimide and a glycine that is amine-protected by a protecting group, at a temperature between about 15° C. and about 30° C., to produce a compound of Formula IIa. The next step is to expose a compound of Formula IIa

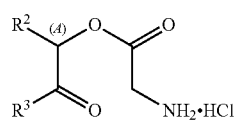

IIa where $R^2$ is isopropyl and $R^3$ is aryl, to acidified ethyl acetate and a trialkylamine such as triethylamine at a temperature between about 15° C. and 30° C., to produce a compound of Formula Ia. The compound of Formula Ia

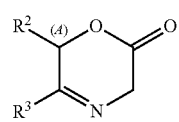

Ia where $R^2$ is isopropyl, $R^3$ is aryl and A is either S or R, is then exposed to 7-octenal, tetra-n-butylammonium bromide and potassium carbonate in dichloromethane or acetonitrile at a temperature between about 0° C. and about 25° C., to produce a compound of Formula Ic. The compound of Formula Ic

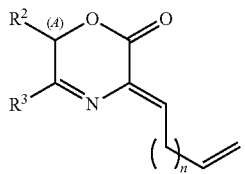

where $R^2$ is isopropyl, $R^3$ is aryl, A is either S or R, and n is 5, is then exposed to trimethyl sulfoxonium chloride and a group I hydride in a dipolar aprotic solvent at a temperature between about 20° C. and about 100° C. to produce a compound of Formula Id. The next step is to expose a compound of Formula Id

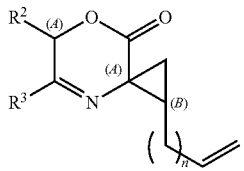

where $R^2$ is isopropyl, $R^3$ is phenyl, A is either S or R, B is R when A is S or B is S when A is R and n is 5, to aqueous NaOH in ethanol to hydrolyze the oxazine ring, and then expose this product to a halide salt of a protecting group in aqueous THF to protect the amine group, to produce a compound of Formula I

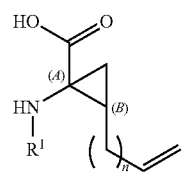

where $R^1$ is a protecting group, A is either S or R, B is R when A is S or B is S when A is R and n is 5.

In a second aspect of the present invention, there is provided a compound of Formula I

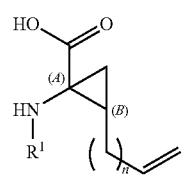

wherein:
$R^1$ is a protecting group;
n is an integer between 1 and 10, and;
A and B are chiral centers such that when A is S, B is R and when A is R, B is S.

The following options may be used in conjunction with the second aspect, either individually or in any suitable combination.

The compound may have an $R^1$ group that is a protecting group removable in a basic solution. It may be Fmoc (fluorenylmethyloxycarbonyl), 9-(2-sulfo)fluorenylmethyl carbamate, Peoc (2-phosphonioethoxycarbonyl), or Ppoc (1-Methyl-1-(triphenylphosphonio) ethyl). The n may be an integer between 1 and 10, or between 1 and 6, 1 and 4, 2 and 6, 2 and 4, 3 and 6 or 4 and 6. It may be any one of 1, 2, 3, 4, 5, 6, 7, 8, 9 or 10. A may be S and B may be R or A may be R and B may be S.

The compound of Formula I may be Fmoc-protected (1S,2R)-1-amino-2-(but-3-en-1-yl)cyclopropane-1-carboxylic acid. It may be Fmoc-protected (1R,2S)-1-amino-2-(hept-6-en-1-yl)cyclopropane-1-carboxylic acid. It may be Fmoc-protected (1R,2S)-1-amino-2-(but-3-en-1-yl)cyclopropane-1-carboxylic acid. It may be Fmoc-protected (1S,2R)-1-amino-2-(hept-6-en-1-yl)cyclopropane-1-carboxylic acid.

In a third aspect of the present invention, there is provided a compound of Formula Ic

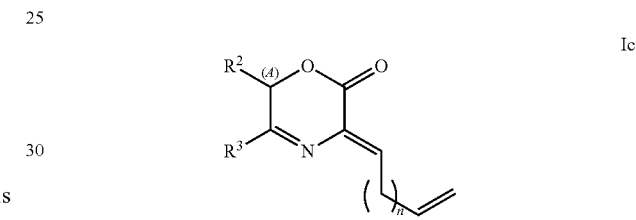

wherein:
$R^2$ is an aliphatic group with a secondary or tertiary carbon atom covalently bonded to the chiral center A;
$R^3$ is aryl or heteroaryl;
n is an integer between 1 and 10, and;
A is a chiral center.

In a fourth aspect of the present invention, there is provided a compound of Formula Id

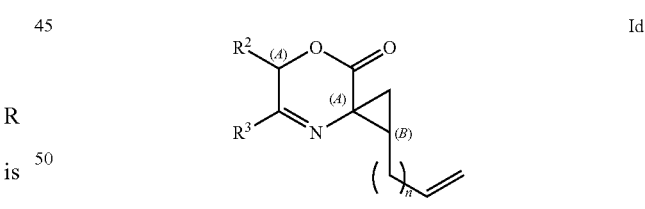

wherein:
$R^2$ is an aliphatic group with a secondary or tertiary carbon atom covalently bonded to the chiral center A;
$R^3$ is aryl or heteroaryl;
n is an integer between 1 and 10, and;
A is a chiral center.

The following options may be used in conjunction with either the third or fourth aspects, either individually or in any suitable combination.

The aliphatic $R^2$ group may be a branched hydrocarbyl group. It may be isopropyl, sec-butyl, tert-butyl or sec-pentyl. The $R^3$ group may be aryl. It may be phenyl.

In a fifth aspect of the present invention, there is provided a use of a compound according to Formula I

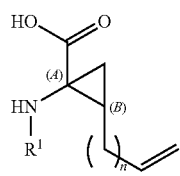

wherein:

$R^1$ is a protecting group;

n is an integer between 1 and 10, and;

A and B are chiral centers such that when A is S, B is R and when A is R, B is S; to synthesize a stapled peptide.

In a sixth aspect of present invention, there is provided a use of a compound of Formula Ia

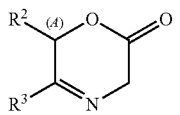

in a reaction with a compound of Formula Ib

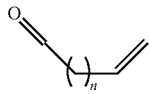

to produce a compound of Formula Ic

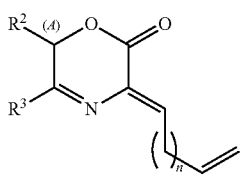

wherein A is a chiral center, $R^2$ is an aliphatic group with a secondary or tertiary carbon atom covalently bonded to the chiral center A, $R^3$ is aryl or heteroaryl and n is an integer between 1 and 10.

In a seventh aspect of the present invention, there is provided a use of a compound of Formula Ic

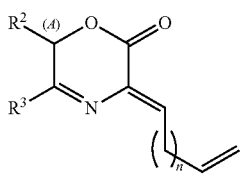

in a reaction with a trialkyl sulfoxonium halide to produce a compound of Formula Id

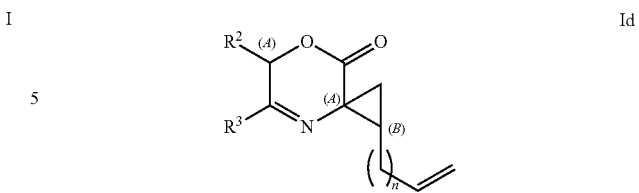

wherein A is a chiral center, $R^2$ is an aliphatic group with a secondary or tertiary carbon atom covalently bonded to the chiral center A, $R^3$ is aryl or heteroaryl and n is an integer between 1 and 10.

In an eighth aspect of the present invention, there is provided a use of a compound of Formula Id

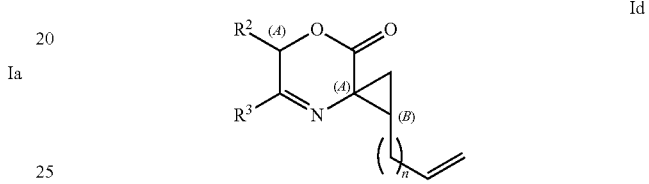

to produce a compound of Formula I

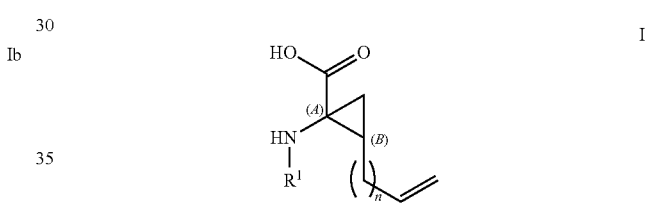

wherein $R^1$ is a protecting group, n is an integer between 1 and 10, A and B are chiral centers such that when A is S, B is R and when A is R, B is S, $R^2$ is an aliphatic group with a secondary or tertiary carbon atom covalently bonded to the chiral center A, and $R_3$ is aryl or heteroaryl.

BRIEF DESCRIPTION OF DRAWINGS

Preferred embodiments of the present invention will now be described, by way of example only, with reference to the accompanying figures, wherein.

DEFINITIONS

Figure 1:
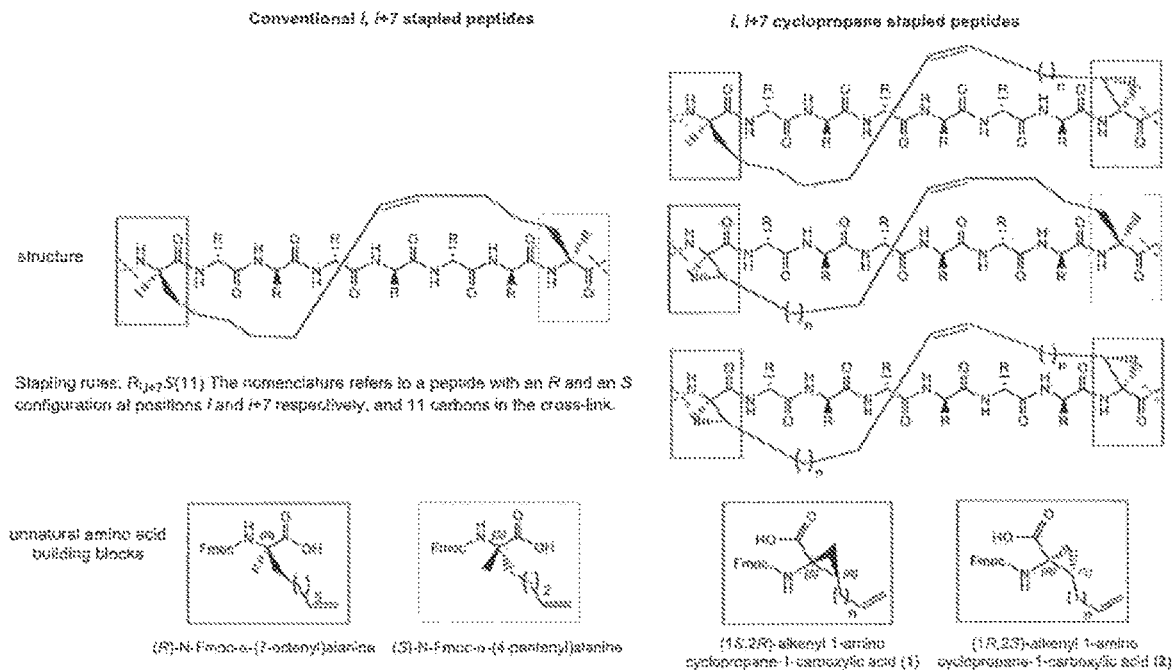
FIG. 1 shows the structure and stereochemistry of ACC building blocks and representative examples of stapled peptides, in which ACC building blocks may be used.
Figure 2:
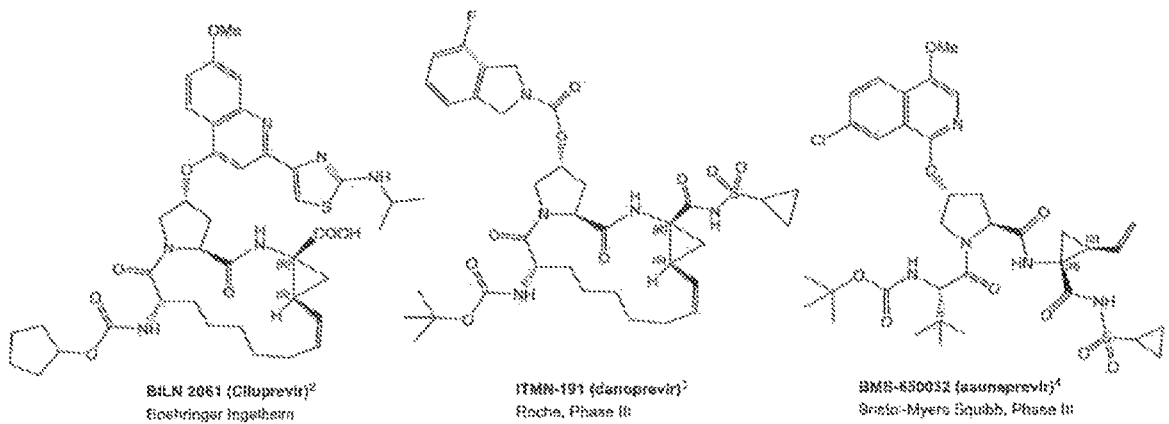
FIG. 2 shows representative HCV NS3/4a protease inhibitors.

The term "ACC" or "ACCs" as used herein means alkenyl 1-aminocyclopropane-1-carboxylic acid, which refers generally to the molecular chassis that is shared by compounds of Formula I.

The term "building blocks" as used herein refers to compounds that may be used as monomers to form a polymeric chain. As used herein, the term "building blocks" more specifically refers to amino acids, whether natural, modified or unnatural, that can be integrated into a peptide chain via regular peptide synthesis methods.

The term "peptidic" as used herein means "of or pertaining to peptides or peptide-like compounds". This term may be used herein interchangeably with the term "peptide". As used herein, "peptidic" will generally be used to refer to a peptide chain that incorporates a modified amino acid or ACC in the chain.

The term "stapled peptides" and the like as used herein refers to peptidic chains that incorporate two (or more) modified amino acids or ACCs, and wherein the alkyl chains of the ACCs have been covalently joined via a reaction to produce an intramolecular linker that constricts the movement or freedom of the peptidic chain in at least one dimension.

The term "protecting group" as used herein refers to any chemical group that is covalently bound to a free amine group to ensure that the amine does not participate in any given reaction, but yet is relatively easily removed once the reaction is completed. Many different types of protecting groups are known in the art and the skilled addressee would be familiar with this concept.

The term "strong base" as used herein refers to a base which completely dissociates into a cation and hydroxide ion in water at a concentration of 1.0M at 25° C. Examples of strong bases include NaOH, LiOH, KOH, RbOH, CsOH, and $NH_4OH$.

The term "alkyl" as used herein refers to a hydrocarbon radical derived from an alkane, which may be linear, branched or cyclised. For instance "methyl" refers to a radical group derived from methane.

The term "aryl" as used herein refers to radical derived from an aromatic hydrocarbon, for instance "phenyl" refers to a radical group derived from benzene. The term "heteroaryl" as used herein refers to a radical derived from an aromatic hydrocarbon, wherein at least one of the aromatic carbon atoms are replaced with a non-carbon heteroatom, such as N, O or S.

The term "room temperature" as used herein refers to a temperature that is between about 15° C. and about 30° C.

The term "comprises" means "includes". Variations on the word "comprises", such as "comprising" and "comprise", have corresponding meanings. As used herein, the terms "including" and "comprising" are non-exclusive. As used herein, the terms "including" and "comprising" do not imply that the specified integer(s) represent a major part of the whole.

The term "consists essentially of" means "to the exclusion of other additional components purposefully added", or "only the following recited elements are intended to be present". Additional components that are in the defined composition or device that are not intentionally present are acceptable.

DESCRIPTION OF EMBODIMENTS

This specification describes an asymmetric preparation of ACCs such as Fmoc-protected (1S,2R)-1-amino-2-(but-3-en-1-yl)cyclopropane-1-carboxylic acid and (1R,2S)-1-amino-2-(hept-6-en-1-yl)cyclopropane-1-carboxylic acid. These unnatural amino acids were primarily designed for incorporation into stapled peptides but the unique conformational properties of these building blocks may also provide structural stability to other systems. The ACCs prepared herein include a cyclopropyl rigidifying element from which the alkenyl linker is attached, which is believed to improve α-helical stabilisation and protease resistance in the stapled peptides.

Key steps of the synthesis include condensation of terminal alkenyl aldehydes with a chiral glycine template followed by an enantioselective Corey-Chaykovsky cyclopropanation. The synthesis described herein is amenable to a range of aldehydes with varying alkenyl chain lengths.

Thus, the present invention relates to the synthesis of building blocks for producing stapled peptides. These building blocks are rigid, unnatural amino acids that may be incorporated into stapled peptides but may also provide structural stability to other peptidic systems. As will be described in greater detail below and with reference to the Examples, the synthesis method of the present invention results in the improved, selective production of asymmetric ACC building blocks for producing stapled peptides.

Building Blocks

The building blocks referred to herein and produced by the synthetic method of the present invention are broadly known as ACCs (alkenyl 1-amino cyclopropane-1-carboxylic acid). They may be broadly defined by Formula I below.

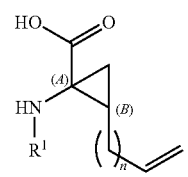

I wherein: $R^1$ is a protecting group; n is an integer between 1 and 10; and A and B are chiral centers such that when A is S, B is R and when A is R, B is S.

As defined in Formula I above, the ACCs of the present invention must have an alkyl chain, the length of which is defined by the variable n. The alkyl chain may be between 1 and 10 carbon atoms in length, or between 1 and 5, 5 and 10, or 3 and 7 (e.g., 1, 2, 3, 4, 5, 6, 7, 8, 9 or 10 carbon atoms in length). The alkyl chain originates on one of the sterically-active carbon atoms of the cyclopropyl group. The alkyl chain terminates with a vinyl moiety, the carbon atoms of which are not included in the total number of alkyl chain carbons described above. This moiety may be used to form a linkage in a stapled peptide. The alkyl chain may act as a linker between the two modified amino acids to be covalently linked in the finished peptide sequence of a stapled peptide. The length of the alkyl chains will be dictated by the separation in space of the two modified amino acids in the stapled peptide chain that are to be joined together.

In the ACCs of the present invention, two chirally-active centres are located on adjacent carbon atoms of the cyclopropanyl group. These two chiral centres must be of opposite configurations. Thus when A is R, B is S, and when A is S, B is R. In use, when the ACC building block is incorporated into a peptidic chain via peptide linkers to the free amine group and free carboxylate group, the chiral centres of opposite configurations work to orientate the alkyenyl chain in such a way so as to allow the free end of the alkenyl chain to be easily bonded, via an intramolecular bond, to another modified amino acid in the same peptidic chain.

As the skilled addressee would be aware, peptide synthesis commonly employs the use of N-terminal protecting groups to reduce or eliminate unwanted side reactions. Hence, the ACCs of Formula I comprise a protecting group bonded to the free amine group and designated herein as $R^1$. The protecting group $R^1$ may be any suitable protecting group known in the art, e.g., it may be Boc, Fmoc, Peoc, Ppoc, 9-(2-sulfo)fluorenylmethyl carbamate, CBZ or any other group capable of protecting the free amine group during peptide synthesis. It may be preferred that the protecting group is removed in pH conditions that are either neutral (e.g. about 7) or basic (e.g. greater than 7, such as about 7, 8, 9, 10, 11, 12, 13 or higher). Thus suitable protecting groups that may be used include Fmoc, Peoc, Ppoc, 9-(2-sulfo)fluorenylmethyl carbamate or any other protecting group capable of being removed in neutral or basic pH conditions.

Examples of compounds of Formula I that are representative of suitable ACC building blocks for stapled peptides include (1S,2R)-1-amino-2-(but-3-en-1-yl)cyclopropane-1-carboxylic acid, (1R,2S)-1-amino-2-(but-3-en-1-yl)cyclopropane-1-carboxylic acid, (1S,2R)-1-amino-2-(hept-6-en-1-yl)cyclopropane-1-carboxylic acid and (1R,2S)-1-amino-2-(hept-6-en-1-yl)cyclopropane-1-carboxylic acid.

Synthesis of ACCs

Compounds of Formula I, as generally defined above, may be synthesised as disclosed below. The following scheme provides an overview of representative, non-limiting embodiments of the invention. The skilled addressee will recognise that analogues may be prepared from analogous starting materials.

General Method:

The preparation of compounds described by Formula I is provided in the general process of Scheme 3 below:

and 6, 2 and 4, 3 and 6, 4 and 6, 2 and 8, 3 and 7, 2 and 9, 3 and 8 or 4 and 7, for example 1, 2, 3, 4, 5, 6, 7, 8, 9, or 10):

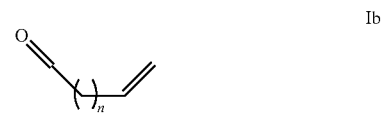

In the general scheme above, the starting material described as Formula IId can be prepared by many methods well known in the art, or it may be obtained commercially. The selection of the chiral centre of Formula IId effectively defines the chirality of the ultimate product, Formula I, whereby A in Formula IId is either R or S, with B of Formula I being the opposite configuration to A (e.g., when A is R, B must be S; when A is S, B must be R). It is believed that the sterically-bulky groups defined by $R^2$ and $R^3$ define the chiral centers of the final cyclopropyl ring of Formula I by directing the attack of the trialkyl sulfoxonium to the plane that is less sterically hindered. In other words, the cyclopropyl ring extends from the plane defined by the 1,4-oxazine ring in the opposite direction that the bulky $R^2$ extends from the same plane, e.g., when the $R^2$ aliphatic group extends below the plane of the 1,4-oxazine ring, the cyclopropyl ring extends above the plane of the 1,4-oxazine ring.

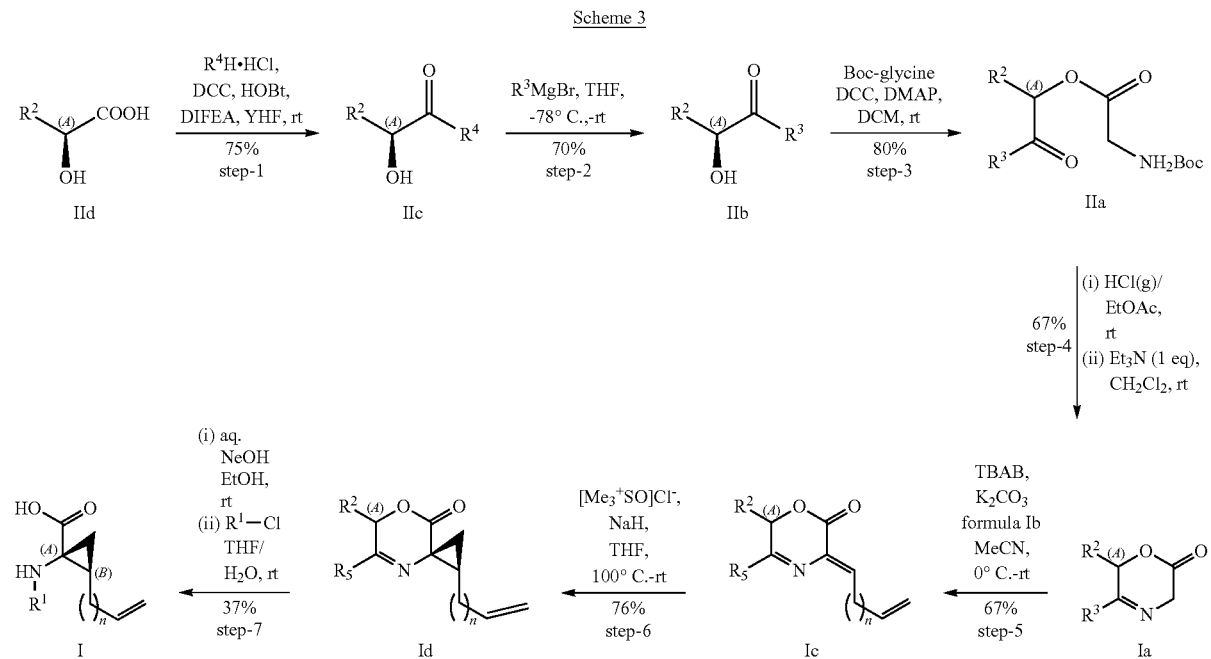

$R^1$ is a functional group used to protect amine nitrogen functionality. $R^2$ is an aliphatic group with a secondary or tertiary carbon atom covalently bonded to the chiral centre A. Examples of $R^2$ include isopropyl, sec-butyl, tert-butyl, isopentyl or sec-pentyl. $R^3$ is an aryl or heteroaryl group, for example phenyl, naphthyl, pyridinyl or pyrazinyl. $R^4$ is a dialkylamino group, in which each alkyl group is independently a methyl, ethyl, propyl or butyl group. Formula Ib is a compound described as shown below, in which n is an integer between 1 and 10 (e.g., between 1 and 6, 1 and 4, 2

In the first step of the scheme, the starting compound of Formula IId is treated with a dialkylamine hydrohalide salt, a base, a catalyst and a dehydrating agent to form a compound of Formula IIc. The dialkylamine hydrohalide salt comprises two alkyl groups, each independently selected from a methyl, ethyl, propyl or butyl group, and a hydrohalide salt, such as HF, HCl, HBr and HI. The base used in this step is a sterically hindered base. In this context a sterically hindered base is taken to be a base that can only react with a proton as any larger chemical species cannot access the basic site. Numerous examples of these are known in the art. For example, the sterically hindered base may be N,N-diisopropylethylamine (DIPEA). The catalyst may be any catalyst which is known to catalyse an amidation reaction, such as hydroxybenzotriazole (HOBt). The dehydrating agent may be a carbodiimide. It may be N,N'-dicyclohexylcarbodiimide (DCC) or it may be (2-(thiophen-2-yl)boronic acid. The solvent in which this reaction occurs may be tetrahydrofuran (THF) or it may be another suitable polar aprotic solvent. The reaction of this step is carried out at a temperature of between about 0° C. and about 25° C. (e.g. between about 0 and about 20° C., or between about 0° C. and 20° C., 0° C. and 15° C., 0° C. and 10° C., 10° C. and 25° C., 10° C. and 20° C., 15° C. and 25° C. or 20° C. and 25° C., for example about 0, 1, 2, 3, 4, 5, 6, 7, 8, 9, 10, 15, 20 or 25° C.).

In the second step of Scheme 3, the amide of Formula Ic is reacted with a Grignard reagent, to substitute the dialkylamino group of the amide, $R^4$, with the $R^3$ aryl or heteroaryl group of the Grignard reagent to form a compound of Formula IIb. The dialkylamino group $R^4$ comprises two alkyl groups. Each of these is independently a methyl, ethyl, propyl or butyl group. The $R^3$ group may be any suitable aryl or heteroaryl group, such as phenyl, naphthyl, pyridyl or pyrimidyl. The Grignard reagent may be an arylmagnesium bromide, for example it may be phenylmagnesium bromide. The reaction of this step is carried out at a temperature of between about −80° C. and about 25° C. (e.g. between about −80° C. and about 20° C., or between about −60° C. and 25° C., −40° C. and 25° C., −20° C. and 25° C., 0° C. and 25° C., 0° C. and 15° C., 0° C. and 10° C., 10° C. and 25° C., 10° C. and 20° C., 15° C. and 25° C. or 20° C. and 25° C., for example about −80, −75, −70, −65, −60, −55, −50, −45, −40, −35, −30, −25, −20, −15, −10, −5, 0, 1, 2, 3, 4, 5, 6, 7, 8, 9, 10, 15, 20 or 25° C.). It may be conducted at an initial temperature of between about −80° C. and about −60° C., or between about −80° C. and about −65° C., −80° C. and −70° C., −78° C. and −68° C. or −75° C. and −65° C. (e.g., about −80° C., −79, −78, −77, −76, −75, −74, −73, −72, −71, −70, −69, −68, −67, −66, −65, −64, −63, −62, −60 or −60° C.) and thereafter allowed to warm to a temperature of between about 15° C. and about 25° C., or between 20° C. and about 25° C. or between about 15° C. and about 20° C. (e.g., about 15, 16, 17, 18, 19, 20, 21, 22, 23, 24 or 25° C.).

Step 3 of Scheme 3 is an esterification reaction involving the product of Step 2, Formula IIb, and glycine, whereby the reaction occurs between the hydroxyl group of Formula IIb and the carboxylic acid group of glycine to form a compound of Formula IIa. This reaction generally is mediated by a nucleophilic catalyst, a coupling reagent and involves a protected glycine. The nucleophilic catalyst may be a basic nucleophilic catalyst. It may be 4-dimethylaminopyridine (DMAP). The coupling agent should be capable of converting carboxylic acids to active esters under mild conditions whilst retaining full chiral integrity. The coupling agent may be DCC, N,N'-diisopropylcarbodiimide (DIC) or 1-ethyl-3-(3-dimethylaminopropyl)carbodiimide (EDC). The protected glycine may be protected by a labile protectant group and is removable in an acid environment. The protectant group on the glycine may be, for example, Boc, Adoc, t-Bumeoc or Adpoc. In the reaction step provided in Scheme 3, DCC is used to activate the carboxylic acid group, rather than the more traditional acid catalyst. This is preferred since an acid catalyst may also remove the Boc-protection from the N-terminal of the glycine and likely lead to low yield and undesirable side reactions occurring. This mild esterification reaction is by way of an example, and other methods known to the skilled person for carrying out an esterification reaction under mild conditions would also be suitable for this method. The reaction of this step is carried out at a temperature of between about 15° C. and about 30° C. (e.g. between about 15° C. and about 25° C., or between about 15° C. and 20° C., 20° C. and 30° C., or 20° C. and 25° C., for example about 15, 16, 17, 18, 19, 20, 21, 22, 23, 24, 25, 26, 27, 28, 29 or 30° C.).

These first three steps are known to the skilled addressee in the production of glycine-derived building blocks for use in the production of stapled peptides. However, the remaining steps in Scheme 3, resulting in the production of a compound of Formula I, have been surprisingly found to result in the favouring of one optical isomer over the other, rather than a racemic mixture.

Step 4 of Scheme 3 involves two reactions occurring sequentially, commonly in a one-pot synthesis. Firstly, the protecting group on the amine of the compound of Formula IIa is removed from the amine group via acid hydrolysis. Whilst hydrochloric acid is shown in Scheme 3, any appropriate acid or catalyst, whether a mineral acid (e.g., HF, HBr, $H_3PO_4$, or $H_2SO_4$), an organic acid (e.g., TFA, TBAF or AcOH) or metal-based catalyst (e.g., $Sn(OTf)_2$ or $Cu(OTf)_2$), can be used to deprotect the amine moiety. Where an acid is used as the catalyst to remove the protecting group, the solvent used may be an organic ester, such as ethyl acetate. The removal of the protecting group results in the formation of the conjugate acid of the compound of Formula IIa.

The second reaction of Step 4 involves a dehydration reaction of the conjugate acid of the compound of Formula IIa, resulting in an intramolecular cyclisation involving the free amine to form the 1,4-oxazine-based compound of Formula Ia. Dichloromethane is shown as the solvent in Scheme 3, although the skilled person would be aware of other similar haloalkyl solvents that could also be used in carrying out this reaction. Importantly, this step involves the use of 1 equivalent of triethylamine. Surprisingly, by limiting the triethylamine reactant to 1 equivalent of the conjugated acid of Formula IIa, undesirable side reactions including hydrolysis of unreacted earlier intermediates may be avoided and a higher yield obtained than the equivalent reaction carried out with the triethylamine in excess. Other trialkylamines may be used in this reaction, whereby each alkyl group is independently selected form the group consisting of methyl, ethyl, propyl, butyl and pentyl. Other bases may also be used for this reaction, including: N-heterocyclic compounds (for example N-1,8-diazabicyclo[5.4.0]undec-7-ene (DBU) or 1,5-diazabicyclo[4.3.0]non-5-ene (DBN)); organolithiums (for example n-butyllithium or tert-butyllithium); pyridine and pyridine derivatives (for example, 4-(diethylamino)pyridine); Grignard reagents (for example, ethylmagnesium bromide or isobutylmagnesium bromide); metal alkoxides (for example, sodium methoxide or sodium tert-pentoxide); or other inorganic bases such as NaOH, $Ca(OH)_2$, LiOH, $CaCO_3$, KOH or $K_2CO_3$. Both reactions of this step are carried out at a temperature of between about 0° C. and about 30° C. (e.g. between about 0° C. and about 25° C., or between about 0 and 20° C., 0° C. and 15° C., 10° C. and 20° C., 15° C. and 20° C., 20° C. and 30° C., or 20° C. and 25° C., for example about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30° C.). It may be conducted at an initial temperature of 0° C. and thereafter allowed to warm to a temperature of between about 20° C. and about 30° C. (e.g., between about 20° C. and 25° C., or between about 25° C. and about 30° C., for example about 20, 21, 22, 23, 24, 25, 26, 27, 28, 29 or 30° C.).

In step 5, the product of Step 4, being a compound of Formula Ia, is reacted via a Knoevenagel condensation reaction with a compound of Formula Ib, catalysed by the combination of tetra-n-butylammonium bromide (TBAB) and K$_2$CO$_3$ in an acetonitrile environment. The reactants shown in this step are provided as an example; other quaternary amine phase-change catalysts and/or catalytic systems utilising a tetraalkylammonium salt could be used by the skilled addressee in carrying out this reaction; alternative basic inorganic salts could be used in conjunction with the quaternary amine phase-change catalyst; and an alternative polar aprotic organic solvent could be used, such as dichloromethane, for example. The reaction of this step is carried out at a temperature of between about 0° C. and about 25° C. (e.g. between about 0° C. and about 20° C., or between about 0° C. and 20° C., 0° C. and 15° C., 0° C. and 10° C., 10° C. and 25° C., 10° C. and 20° C., 15° C. and 25° C. or 20° C. and 25° C., for example about 0, 1, 2, 3, 4, 5, 6, 7, 8, 9, 10, 15, 20 or 25° C.).

Step 6 of Scheme 3 involves an enantioselective, chiral-auxiliary mediated Corey-Chaykovsky cyclopropanation reaction at the double bond that was added to the oxazine ring moiety in the compound of Formula Ic in Step 5. Surprisingly, it was found that the use of trimethyl sulfoxonium iodide and sodium hydride in acetonitrile, which is a previously published method for carrying out similar reactions, were not successful. However, and as shown in Scheme 3, the use of trimethyl sulfoxonium chloride in THF under reflux conditions provided the desired cyclopropanyl adduct in good yield and selectivity. As the skilled addressee would be aware, other trialkyl sulfoxonium halides may be used, wherein the halide is selected from fluorine, chlorine and bromine. As mentioned above, the iodide salts of the trialkyl sulfoxonium halides are unlikely to be effective. The trialkyl sulfoxonium halides may also have each of the three alkyl groups independently selected from methyl, ethyl, propyl, butyl and pentyl, although one alkyl group must be methyl. Further, whilst sodium hydride is used in Scheme 3 above, any other group I hydride, such as LiH or KH may be used. The solvent in which this reaction occurs in Scheme 3 is THF, but any other polar aprotic solvent able to dissolve the reactants may be used, such as acetonitrile or acetone, as understood by the skilled addressee. The reaction of this step is carried out at a temperature of between about 20° C. and about 100° C. (e.g. between about 20° C. and about 80° C., or between about 30° C. and 70° C., 40° C. and 80° C., 50° C. and 90° C., 30° C. and 60° C., 40° C. and 60° C., 20° C. and 50° C. or 30° C. and 50° C., for example about 20, 25, 30, 35, 40, 45, 50, 55, 60, 65, 70, 75, 80, 85, 90, 95 or 100° C.).

The final step of Scheme 3 involves two sequential reactions, commonly in a one-pot synthesis. Firstly, a compound of Formula Id is treated with a solution of an aqueous strong base in an alcohol solvent, which hydrolyses the 1,4-oxazine chassis at the heteroatoms to produce an alkenyl cyclopropyl-modified glycine compound. This glycine derivative has a non-protected amine group. Whilst aqueous NaOH and EtOH are shown in Scheme 3, any strong base (such as LiOH, KOH or NH$_4$OH) and any polar protic organic solvent could be used to perform this reaction step. Importantly, this step of cleaving the modified glycine compound from the steric template was surprisingly found to be more successful with a strong base, rather than under acidic conditions which had been earlier reported as being successful for similar modified glycine precursors. Indeed, when acidic conditions are used, complete hydrolysis is not achieved, with basic conditions the most successful.

Secondly, the free amine site is then protected in reaction (ii) of Step 7 by the addition of the salt of a protecting group, shown as R$^1$—Cl in Scheme 3, however any suitable amine protecting group that is also suitable for peptide synthesis could be used, such as but not limited to, Boc, Fmoc, Peoc, Ppoc, 9-(2-sulfo)fluorenylmethyl carbamate, as understood by the skilled addressee. The salt of the protecting group added to the reaction mixture may be a chloride or may be any other suitable salt, such as the fluoride, bromide or iodide salt. The protecting group salt added to the reaction mixture is dissolved in aqueous THF in Scheme 3, although any aprotic polar solvent may be used.

The steps of the above general scheme are generally conducted discretely, i.e., not as a 'one-pot' synthesis in that the product is collected at the completion of each reaction step and may or may not be purified after collection. In steps that comprise multiple (e.g., more than one) reactions, the product is only collected at the end of the final reaction of that step, as these reactions are carried out sequentially in the same 'pot'. The products may be collected as a crude product, whereby reactants either from the present step or earlier steps, undesired side reaction products and some solvents or other materials may be present in the crude product. Such impurities may then be present as starting materials for the subsequent step. However, the use of crude products may be desirable, due to losses that may incidentally occur during the purification process. Alternatively, the products at the end of each complete step may be collected as a crude product and then purified to remove any excess reactant, solvent and/or undesired side-product that may be present in the crude product. This purification step may include passing the crude product through a silica or fluorinated silica column and collecting the fraction containing the desired product. Products of steps in this reaction scheme that include multiple reactions (e.g., steps 4 and 7) would commonly only be purified after the final reaction (i.e., step (ii)), as these reactions are conducted sequentially in the same reactant vessel.

Intermediary Compounds

The present invention also provides compounds of particular formula that are intermediary compounds of Scheme 3. For example, the present invention provides compounds of Formula Ic:

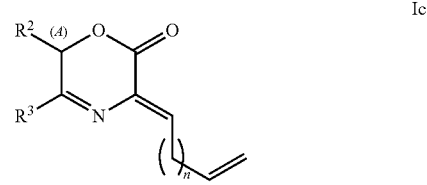

wherein R$^2$ is an aliphatic group with a secondary or tertiary carbon atom covalently bonded to the chiral center A; R$^3$ is an aryl or heteroaryl group; n is an integer between 1 and 10; and A is a chiral center that may be either R or S.

Compounds of Formula Ic must have an alkyl chain, the length of which is defined by the variable n. The alkyl chain may be between 1 and 10 carbon atoms in length (e.g., 1, 2, 3, 4, 5, 6, 7, 8, 9 or 10 carbon atoms in length). The length of the alkyl chain of Formula Ic is the same as the length of the alkyl chain in the ultimate product, Formula I. The alkyl chain originates on one of the sterically-active carbon atoms of the cyclopropyl group. The alkyl chain terminates with a vinyl moiety, the carbon atoms of which are not included in the total number of alkyl chain carbons described above.

Compounds of Formula Ic also comprise an $R^2$ group covalently bonded to the carbon that is the steric center and an $R^3$ group covalently bonded to the ring carbon adjacent to the chiral center. The $R^2$ group is an aliphatic group with a secondary or tertiary carbon atom covalently bonded to the chiral centre A. Examples of $R^2$ include isopropyl, sec-butyl, tert-butyl, isopentyl or sec-pentyl. The $R^3$ group is an aryl or heteroaryl group, for example phenyl, pyridinyl or pyrazinyl.

The present invention also provides compounds of Formula Id:

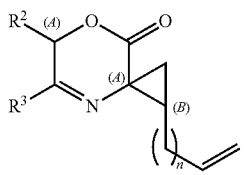

Id wherein $R^2$ is an aliphatic group with a secondary or tertiary carbon atom covalently bonded to the chiral center A; $R^3$ is an aryl or heteroaryl group; n is an integer between 1 and 10; and A and B are opposing chiral centers, wherein when A is R, B is S, or when A is S, B is R.

The variables $R^2$, $R^3$ and n are as defined above for intermediary compound Ic.

Whilst not retained in the final product Formula I, the skilled addressee would understand that the sterically-bulky groups defined by $R^2$ and $R^3$ assist in defining the chiral centers of the final cyclopropyl ring of Formula I by directing the attack of the trialkyl sulfoxonium to the plane that is less sterically hindered. In other words, the cyclopropyl ring extends from the plane defined by the 1,4-oxazine ring in the opposite direction that the bulky $R^2$ extends from the same plane, e.g., when the cyclopropyl ring extends above the plane of the 1,4-oxazine ring, the $R^2$ aliphatic group extends below the plane of the 1,4-oxazine ring.

As would be abundantly clear to the skilled addressee, compounds of Formula Ic are used to produce compounds of Formula Id. Likewise, compounds of Formula Id are used to produce compounds of Formula I.

Use for ACC Building Blocks

Once produced and isolated, compounds of Formula I may be used to produce stapled peptides. Stapled peptides refer to a relatively new class of compounds, whereby the peptide comprises an intramolecular linker between two different residues on the same peptidic chain. The linker essentially constrains the peptide to a particular structure, or at least reduces the freedom of the constrained residues and those residues that are between the constraining residues, from moving, although the degree of freedom available to the peptidic chain will depend on a number of factors, including the size of the peptidic chain, the number of residues that are constrained by the linker, and the ability of the chain sequence to be able to fold up (i.e., the secondary structure of the peptide chain before or after stapling.

Hence, compounds of Formula I, once deprotected to expose the free amine group, include the following common aspects:

an amine group and a carboxylic acid group separated by a carbon group, indicative of naturally occurring amino acids;

a cyclopropyl ring as the amino acid side chain, which is not naturally found as an amino acid side chain; and an alkyl chain that terminates in an alkylene group extending from the cyclopropyl group.

These three general parts of the ACC building blocks all provide specific functions:

the amino acid functionality allows for the ACC building blocks to be inserted into a peptide chain that otherwise comprises naturally occurring amino acids, although it is not necessary to produce peptidic chains that only comprise naturally occurring amino acids other than the modified stapling residues;

the cyclopropyl group, as mentioned above, directs the alkyl chain above the plane of the peptide linkers of that residue and towards a candidate amino acid residue in the chain to which the alkyl chain can be bonded and hence the peptide chain constrained; and the alkyl chain, when covalently bound to another residue in the same peptide chain, creates the constraining linker that restricts the movements of the peptide chain, as the only way to overcome the linker is to break carbon-carbon single bonds.

One use for the compounds of Formula I is in the production of stapled peptides. As the skilled addressee would appreciate, there are two steps to creating a stapled peptide: (1) form a peptide chain with at least two modified residues able to be covalently linked; and (2) link the two modified residues together covalently.

Regarding step (1), a peptide chain is first formed. As the compounds of Formula I are modified amino acids, they can be used in standard peptide synthesis methods that are well-known in the art. The ACC building blocks of the present invention can be added in to a peptide chain, using the same reactants and reaction conditions, in the same manner as any other residue to be added to the peptide chain.

Once the peptide chain is formed, it will commonly contain two ACC residues a defined distance apart. For instance, the modified residues may be separated by 6 amino acid residues to form a i, i+7 stapled peptide, or they may be separated by 4 amino acid residues to form a i, i+5 stapled peptide. Other appropriate arrangements of residues will be known by the skilled addressee, or may become known.

Once the peptide chain is formed, a further reaction joins the two alkyl chains together, which both terminate in alkene moieties.

The present invention may be better understood by the skilled addressee with reference to the following illustrative, and non-limiting, examples.

EXAMPLES

1. Synthesis of (1S,2R)-1-amino-2-(but-3-en-1-yl)cyclopropane-1-carboxylic acid

By way of example, the following is a method for the production of (1S,2R)-1-amino-2-(but-3-en-1-yl)cyclopropane-1-carboxylic acid, a compound within the scope of Formula I. References herein to steps refers to the equivalent step of Scheme 3 above.

Step 1: To a magnetically stirred mixture of equimolar (508 mmol) amounts of (S)-2-hydroxy-3-methylbutyric acid (Formula IId), dimethylamine hydrochloride and hydroxybenzotriazole (HOBt) in 300 mL of tetrahydrofuran (THF), was added an equimolar amount of N,N-diisopropylethylamine (DIPEA) dropwise. After 2 minutes, a slight excess (533 mmol) of N,N'-dicyclohexylcarbodiimide (DCC) was added at once, and the mixture stirred overnight at room temperature. The formed precipitate was filtered and washed with ethyl acetate. The combined filtrates were concentrated under vacuum and filtered through a pad of celite. The solvent was evaporated in vacuo and the residue was purified by flash column chromatography eluting with 0-20% ethyl acetate in hexane to produce (S)-2-hydroxy-3,N,N-trimethylbutanamide (Formula IIc).

Step 2: To a 303 mmol solution of (S)-2-hydroxy-3,N,N-trimethylbutanamide (Formula IIc) in 200 mL of THF was added dropwise an excess 757.5 mmol of phenylmagnesium bromide (3 M in ether) at −78° C. under argon. The mixture was stirred for 16 hours allowing the temperature to rise to room temperature. The reaction was quenched with saturated $NH_4Cl$ and water before extraction with ethyl acetate. The organics were dried with $Na_2SO_4$, filtered and evaporated in vacuo. The crude compound was purified by flash column chromatography eluting with 0-5% ethyl acetate in hexane to afford (S)-α-hydroxyisovalerophenone (Formula IIb).

Step 3: To a solution of DCC (191.5 mmol), N-Boc-glycine (174 mmol) and a catalytic amount of N,N-(dimethylamino)pyridine (DMAP) in 300 mL dichloromethane (DCM) at 0° C., was added a 174 mmol solution of (S)-α-hydroxyisovalerophenone (Formula IIb). The mixture was stirred overnight at room temperature and filtered through a pad of celite. The filtrate was concentrated in vacuo and the crude compound was purified by flash column chromatography eluting with 0-10% ethyl acetate in hexane to produce (1S)-1-benzoyl-2-(tert-butoxycarbonylamino)-2-methylpropyl ethanoate (Formula IIa).

Step 4: (i) A solution of HCl in ethyl acetate (2 M, 200 mL) was added to a solution of (1S)-1-benzoyl-2-(tert-butoxycarbonylamino)-2-methylpropyl ethanoate (Formula IIa) in ethyl acetate (50 mL) at 0° C. and the mixture was stirred at room temperature for 24 hours. The solvent was evaporated under vacuum, and the solid was washed with ether and filtered. (ii) The solid was dissolved in 160 mL of DCM and 1 equivalent of triethylamine was added with stirring at 0° C. The mixture was stirred for 48 hours allowing the temperature to rise to room temperature. The reaction mixture was concentrated in vacuo and the crude compound was purified by fluorinated silica column chromatography eluting with 0-20% ethyl acetate in hexane to afford (6S)-6-isopropyl-5-phenyl-3,6-dihydro-2H-1,4-oxazin-2-one (Formula Ia).

Step 5: A heterogeneous mixture at 0° C. of crude (6S)-6-isopropyl-5-phenyl-3,6-dihydro-2H-1,4-oxazin2-one (Formula Ia) (36.86 mmol), tetrabutylammonium bromide (TBAB) (7.37 mmol) and finely ground $K_2CO_3$ (110.59 mmol) in acetonitrile (80 mL) was stirred for 15 min. To this solution, 4-pentenal (Formula Ib) (47.92 mmol) was added drop wise and the reaction mixture was stirred for 2 hours at room temperature. The mixture was filtered through a pad of celite and the solvent removed under vacuum. The crude compound was purified by flash column chromatography eluting with 0-10% ethyl acetate in hexane to afford (6S)-6-isopropyl-5-phenyl-3-[(Z)-4-pentenylidene]-3,6-dihydro-2H-1,4oxazin-2-one (Formula Ic).

Step 6: Trimethylsulfoxonium chloride (14 mmol) was added to a suspension of NaH (42.25 mmol in mineral oil) in 180 mL of dry THF at 0° C. and the resulting reaction mixture was refluxed at 100° C. for 16 hours. After cooling to room temperature, the suspended solution was syringed out and added to an ice cold solution of 14.08 mmol (6S)-6-isopropyl-5-phenyl-3-[(Z)-pentylidene]-3,6-dihydro-2H-1,4oxazin-2-one (Formula Ic) in THF (40 mL). The reaction mixture was stirred at 0° C. for 1 hour then warmed to room temperature for another hour. The reaction mixture was concentrated in vacuo and the crude compound was purified by flash column chromatography eluting with 0-10% ethyl acetate in hexane to produce a compound of (1R,3S,6S)-1-(but-3-en-1-yl)-6-isopropyl-7-phenyl-5-oxa-8-azz-spiro[2.5]oct-7-en-4-one (Formula Id).

Step 7: (i) A solution of NaOH (53.69 mmol) in water (48 mL) was added to a solution of 10.74 mmol (1R,3S,6S)-1-(but-3-en-1-yl)-6-isopropyl-7-phenyl-5-oxa-8-azo-spiro [2.5]oct-7-en-4-one (Formula Ib) in EtOH (48 mL) The mixture was stirred at room temperature for 2 days, resulting in a crude product containing (1S,2R)-1-amino-2-(but-3-en-1-yl)cyclopropane-1-carboxylic acid. The crude product was treated with 1.5 equivalents of Fmoc-Cl dissolved in a 1:1 THF:water solution (96 mL) with stirring at room temperature for 16 hours. The reaction mixture was acidified to pH 6 using dilute HCl and the product was extracted with ethyl acetate. The combined organics were dried over $Na_2SO_4$ and concentrated in vacuo. The crude compound was purified by neutral silica gel column chromatography eluting with 40-100% ethyl acetate in hexane to afford Fmoc-protected (1S,2R)-1-amino-2-(but-3-en-1-yl)cyclopropane-1-carboxylic acid (Formula I).

A schematic representation of this synthesis is shown below (Scheme 4):

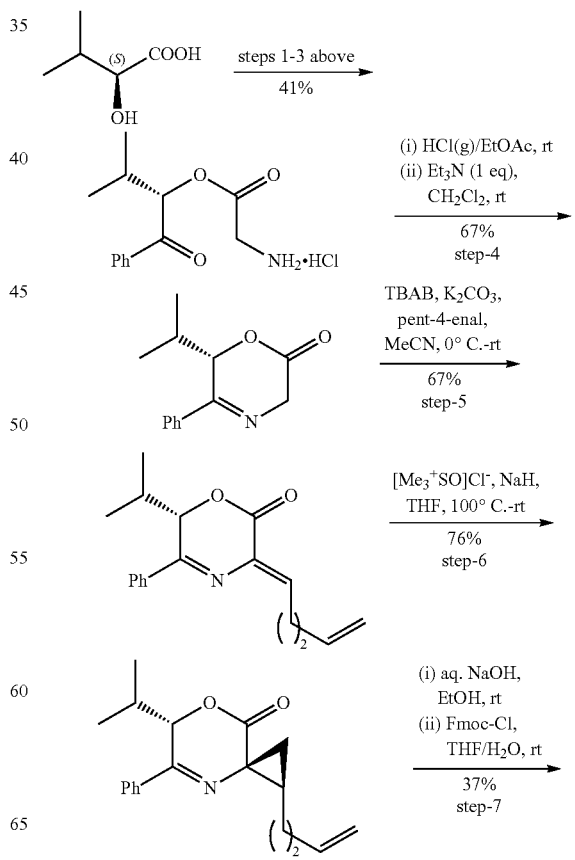

-continued

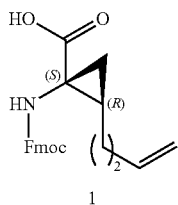

1

2. Synthesis of (1R,2S)-1-amino-2-(hept-6-en-1-yl)cyclopropane-1-carboxylic acid By way of example, the following is a method for the production of (1R,2S)-1-amino-2-(hept-6-en-1-yl)cyclopropane-1-carboxylic acid, a compound within the scope of Formula I. References herein to steps refers to the equivalent step of Scheme 3 above.

Step 1: To a magnetically stirred mixture of equimolar (245.7 mmol) amounts of (R)-2-hydroxy-3-methylbutyric acid (Formula IId), dimethylamine hydrochloride and hydroxybenzotriazole (HOBt) in 150 mL of tetrahydrofuran (THF), was added an equimolar amount of N,N-diisopropylethylamine (DIPEA) dropwise. After 2 minutes, a slight excess (258 mmol) of N,N'-dicyclohexylcarbodiimide (DCC) was added at once, and the mixture stirred overnight at room temperature. The formed precipitate was filtered and washed with ethyl acetate. The combined filtrates were concentrated under vacuum and filtered through a pad of celite. The solvent was evaporated in vacuo and the residue was purified by flash column chromatography eluting with 0-20% ethyl acetate in hexane to produce (R)-2-hydroxy-3,N,N-trimethylbutanamide (Formula IIc).

Step 2: To a 206.8 mmol solution of (R)-2-hydroxy-3,N,N-trimethylbutanamide (Formula IIc) in 450 mL of THF was added dropwise an excess 517 mmol) of phenylmagnesium bromide (3 M in ether) at −78° C. under argon. The mixture was stirred for 16 hours allowing the temperature to rise to room temperature. The reaction was quenched with saturated NH$_4$Cl and water and extracted with ethyl acetate. The organics were dried with Na$_2$SO$_4$, filtered and evaporated in vacuo. The crude compound was purified by flash column chromatography eluting with 0-3% methanol in DCM to afford (R)-α-hydroxyisovalerophenone (Formula IIb).

Step 3: To a solution of DCC (160.6 mmol), N-Boc-glycine (146 mmol) and a catalytic amount of N,N-(dimethylamino)pyridine (DMAP) in 300 mL dichloromethane (DCM) at 0° C. was added a 146 mmol solution of (R)-α-hydroxyisovalerophenone (Formula IIb). The mixture was stirred overnight at room temperature and filtered through a pad of celite. The filtrate was concentrated in vacuo and the crude compound was purified by flash column chromatography eluting with 0-10% ethyl acetate in hexane to produce (1R)-1-benzoyl-2-(tert-butoxycarbonylamino)-2-methylpropyl ethanoate (Formula IIa).

Step 4: (i) A solution of HCl in ethyl acetate (2 M, 250 mL) was added to a solution of (1R)-1-benzoyl-2-(tert-butoxycarbonylamino)-2-methylpropyl ethanoate (Formula IIa) in ethyl acetate (50 mL) at 0° C. and the mixture was stirred at room temperature for 24 hours. The solvent was evaporated under vacuum, and the solid was washed with ether and filtered. (ii) The solid was dissolved in 100 mL of DCM and 1 equivalent of triethylamine was added with stirring at 0° C. The mixture was stirred for 48 hours allowing the temperature to rise to room temperature. The reaction mixture was concentrated in vacuo and the crude compound was purified by fluorinated silica column chromatography eluting with 0-20% ethyl acetate in hexane to afford (6R)-6-isopropyl-5-phenyl-3,6-dihydro-2H-1,4-oxazin-2-one (Formula Ia).

Step 5: A heterogeneous mixture at 0° C. of crude (6R)-6-isopropyl-5-phenyl-3,6-dihydro-2H-1,4-oxazin2-one (Formula Ia) (18.43 mmol), tetrabutylammonium bromide (TBAB) (18.43 mmol), finely ground K$_2$CO$_3$ (55.29 mmol) in DCM (40 mL) was stirred for 15 min. To this solution, 7-octenal (Formula Ib) (27.64 mmol) was added drop wise and the reaction mixture was stirred for 2 hours at room temperature. The mixture was filtered through a pad of celite and the solvent removed under vacuum. The crude compound was purified by flash column chromatography eluting with 0-10% ethyl acetate in hexane to afford (6R)-6-isopropyl-5-phenyl-3-[(E)-7-octenylidene]-3,6-dihydro-2H-1,4oxazin-2-one (Formula Ic).

Step 6: Trimethylsulfoxonium chloride (32.03 mmol) was added to a suspension of NaH (32.03 mmol in mineral oil) in 60 mL of dry THF at 0° C. and the resulting reaction mixture was refluxed at 100° C. for 16 hours. After cooling to room temperature, the suspended solution was syringed out and added to an ice cold solution of 10.76 mmol (6R)-6-isopropyl-5-phenyl-3-[(E)-7-octenylidene]-3,6-dihydro-2H-1,4oxazin-2-one (Formula Ic) in THF (20 mL). The reaction mixture was stirred at 0° C. for 1 hour then warmed to room temperature for another hour. The reaction mixture was concentrated in vacuo and the crude compound was purified by column chromatography eluting with 0-10% ethyl acetate in hexane to produce a compound of (1S,3R,6R)-1-(hept-6-en-1-yl)-6-isopropyl-7-phenyl-5-oxa-8-azo-spiro[2.5]oct-7-en-4-one (Formula Id).

Step 7: (i) A solution of NaOH (24.33 mmol) in water (25 mL) was added to a solution of 4.86 mmol (1R,3S,6S)-1-(hept-6-en-1-yl)-6-isopropyl-7-phenyl-5-oxa-8-azo-spiro[2.5]oct-7-en-4-one (Formula Ib) in EtOH (25 mL) The mixture was stirred at room temperature for 2 days, resulting in a crude product containing (1R,2S)-1-amino-2-(hept-6-en-1-yl)cyclopropane-1-carboxylic acid. The crude product was treated with 1.5 equivalents of Fmoc-Cl dissolved in a 1:1 THF:water solution (50 mL) with stirring at room temperature for 16 hours. The reaction mixture was acidified to pH 6 using dilute HCl and the product was extracted with ethyl acetate. The combined organics were dried over Na$_2$SO$_4$ and concentrated in vacuo. The crude compound was purified by flash column chromatography eluting with 30-100% ethyl acetate in hexane to afford (1R,2S)-1-amino-2-(hept-6-en-1-yl)cyclopropane-1-carboxylic acid (Formula I).

A schematic representation of this synthesis is shown below (Scheme 5):

Scheme 5

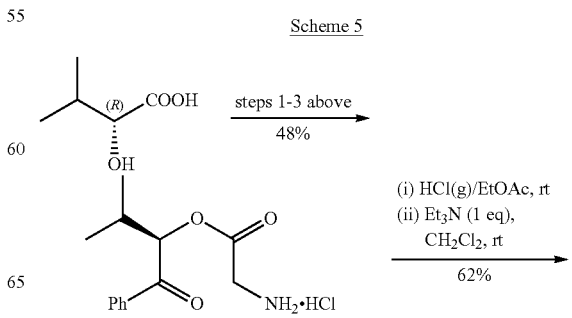

-continued

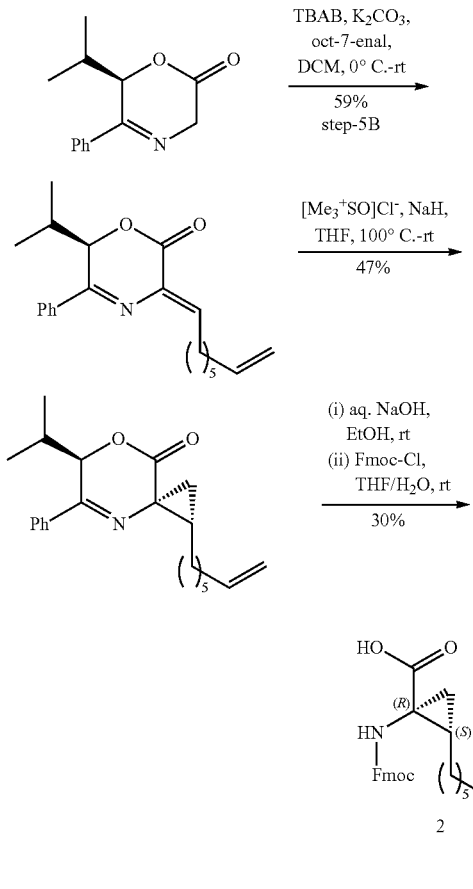

2

The invention claimed is:

1. A method for producing a compound of Formula I

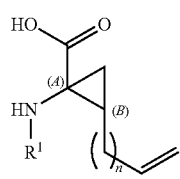

wherein:

R¹ is a protecting group;

n is an integer between 1 and 10, and;

A and B are chiral centers such that when A is S, B is R and when A is R, B is S;

said method comprising the steps of:

a) condensing a chiral compound of Formula Ia

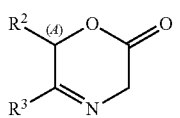

with a compound of Formula Ib

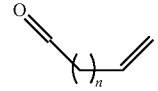

to produce a compound of Formula Ic

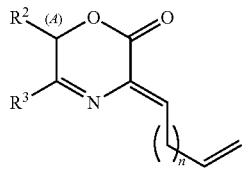

wherein A is a chiral center, R² is an aliphatic group with a tertiary or quaternary carbon atom covalently bonded to the chiral center A, and R³ is aryl or heteroaryl;

b) reacting the non-terminal carbon-carbon double bond formed in step a) to produce a cyclopropyl group, so as to form a compound of Formula Id and;

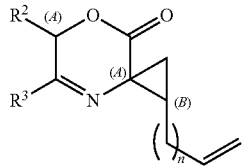

c) hydrolyzing the compound of Formula Id and protecting a free amine produced by the hydrolysis with a reagent comprising R¹ to produce the compound of Formula I.

2. The method of claim 1 wherein:
R¹ is a protecting group which is removable in a basic solution; and/or
R² is a branched hydrocarbyl group; and/or
R³ is aryl; and/or
n is an integer between 1 and 6; and/or
A is S and B is R or A is R and B is S.

3. The method of claim 1, wherein step a) is conducted in the presence of a catalyst and a base, wherein the catalyst is a quaternary ammonium salt and the base is a basic inorganic salt.

4. The method of claim 3, wherein the catalyst is a tetraalkylammonium salt.

5. The method of claim 3, wherein the catalyst is tetra-n-butylammonium bromide.

6. The method of claim 3, wherein step a) is conducted in a dipolar aprotic solvent and at a temperature between 0° C. and 25° C. and step b) is conducted at a temperature between 20° C. and 100° C.

7. The method of claim 1, wherein step b) comprises the reaction of compound Ic with a trialkyl sulfoxonium halide, in the presence of a group I hydride and an organic solvent, wherein:
the trialkyl sulfoxonium halide species comprises three alkyl groups independently selected from methyl, ethyl, propyl, butyl and pentyl, wherein at least one alkyl group is methyl; and/or
the halide group of the trialkyl sulfoxonium halide species is selected from the group comprising fluoride, chloride, bromide and iodide, optionally wherein the trialkyl sulfoxonium halide species is trimethyl sulfoxonium chloride; and/or wherein the group I hydride is LiH, NaH or KH; and/or wherein the organic solvent is a polar aprotic solvent, optionally wherein the organic solvent is tetrahydrofuran.

8. The method of claim 1, wherein step c) comprises exposing the compound of Formula Id to an aqueous strong base and a compound of general formula $R^1X$, wherein $R^1$ is as defined in claim 1, X is a halogen selected from fluorine, chlorine, bromine and iodine, and the strong base is LiOH, NaOH, KOH or $NH_4OH$, and wherein step c) is conducted at room temperature.

9. The method of claim 1, further comprising the step of preparing the compound of Formula Ia by carrying out a dehydration reaction of a compound of Formula IIa

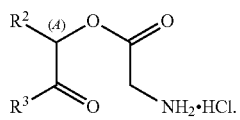

IIa to form an oxazine ring, wherein the dehydration reaction comprises exposing the compound of Formula Ia to a trialkylamine, wherein the trialkylamine comprises three alkyl groups, each independently selected from the group comprising methyl, ethyl, propyl and butyl, and wherein the dehydration reaction is conducted at room temperature in an acidified organic solvent, wherein the acidified organic solvent is an acidified organic ester and comprises HF, HCl, HBr or HI.

10. The method of claim 9, wherein about one molar equivalent of the trialkylamine is used when compared to the amount of conjugate acid of Formula IIa that is present.

11. The method of claim 9, further comprising a step of preparing the compound of Formula IIa, said step comprising the addition of a protected glycine compound to a compound of Formula IIb

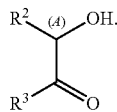

IIb wherein the protected glycine compound comprises a covalently bound protecting group.

12. The method of claim 11, wherein the glycine is added by exposing a compound of Formula IIa to a nucleophilic catalyst, a coupling agent and the protected glycine compound, wherein:

the nucleophilic catalyst is a basic nucleophilic catalyst; and/or the coupling agent is capable of converting carboxylic acids to activated esters; and/or the protecting group is an acid labile protecting group.

13. The method of claim 11, wherein the reaction is conducted at room temperature.

14. The method of claim 11, further comprising a step of preparing the compound of Formula IIb by conducting a reaction between a compound of Formula IIc

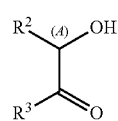

IIc wherein $R^4$ is a dialkylamino group, and a Grignard reagent of general formula $R^3MgBr$ in an organic ether solvent, optionally:

wherein the dialkylamino group of $R^4$ comprises two alkyl groups, each independently selected from the group comprising methyl, ethyl, propyl and butyl; and/or the Grignard reagent is arylmagnesium bromide, optionally wherein the Grignard reagent is phenylmagnesium bromide.

15. The method of claim 14, wherein the reaction begins at a temperature of −78° C. and rises to room temperature during the reaction.

16. The method of claim 14, further comprising a step preparing the compound of Formula IIc by performing an amidation reaction on a compound of Formula IId

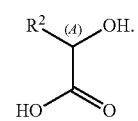

IId wherein the amidation reaction is conducted by exposing a compound of Formula IId to a base, a catalyst, a coupling agent and a dialkyamine hydrohalide salt, wherein:

the dialkyamine hydrohalide salt is of general formula $R^4H.HX$, wherein $R^4$ is a dialkylamino group comprising two alkyl groups, and each alkyl group is independently selected from the group comprising methyl, ethyl, propyl and butyl, and X is a halogen; and/or the dehydrating agent is N,N'-dicyclohexylcarbodiimide or (2-(thiophen-2-yl)phenyl)boronic acid; and/or the catalyst is hydroxybenzotriazole; and/or the base is a sterically hindered base.

17. A compound of Formula I

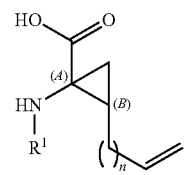

I wherein:

$R^1$ is a protecting group;

n is an integer between 1 and 10, and;

A and B are chiral centers such that when A is S, B is R and when A is R, B is S.

18. A compound according to claim 17, wherein $R^1$ is a protecting group removable in a basic solution.

19. A compound of Formula I according to claim 18 being selected from the group consisting of: Fmoc-protected (1S, 2R)-1-amino-2-(but-3-en-1-yl)cyclopropane-1-carboxylic acid; Fmoc-protected (1R,2S)-1-amino-2-(hept-6-en-1-yl)

cyclopropane-1-carboxylic acid; Fmoc-protected (1R,2S)-1-amino-2-(but-3-en-1-yl)cyclopropane-1-carboxylic acid; and Fmoc-protected (1S,2R)-1-amino-2-(hept-6-en-1-yl)cyclopropane-1-carboxylic acid.

* * * * *

UNITED STATES PATENT AND TRADEMARK OFFICE
CERTIFICATE OF CORRECTION

PATENT NO. : 11,091,427 B2
APPLICATION NO. : 16/497299
DATED : August 17, 2021
INVENTOR(S) : Yuen et al.

Page 1 of 2

It is certified that error appears in the above-identified patent and that said Letters Patent is hereby corrected as shown below:

On the Title Page

(71) Applicant: Insert -- Greg Verdine, Cambridge, MA (US) --

(56) OTHER PUBLICATION, Column 2, Line 3, Hilinski et al. cite: Delete "Stitchedf" and insert -- Stitched --

In the Specification

Column 1, Line 27, Scheme 1: Delete "Alcalase 2.1 L" and insert -- Alcalase 2.4 L --

Column 2, Line 63, Scheme 2: Delete "$H_2N^+$" and insert -- $H_3N^+$ --

Column 7, Line 36: Delete "$R^4H.HX$" and insert -- $R^4H·HX$ --

Column 17-18, Scheme 3: Delete Scheme 3 and replace with the following:

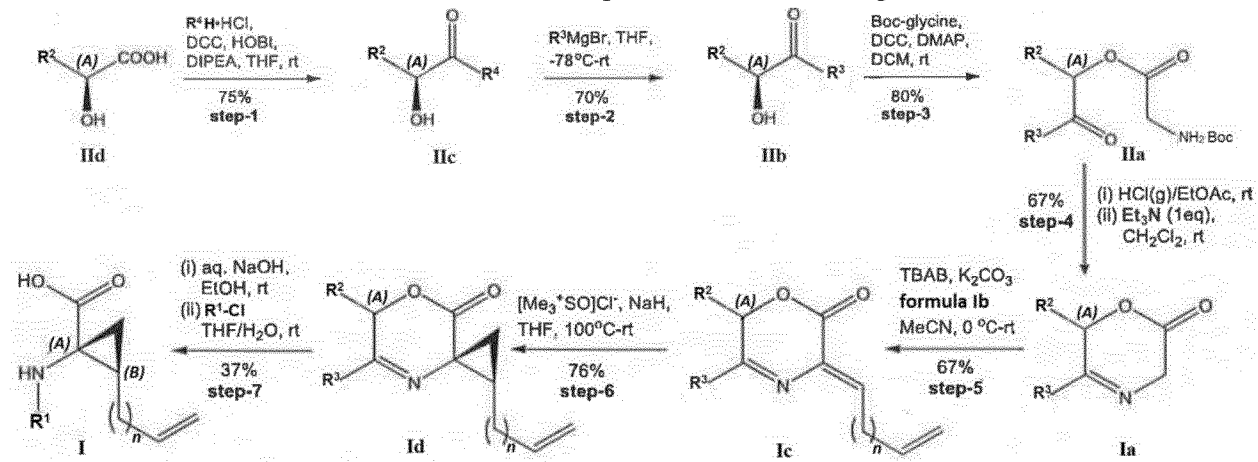

Scheme 3

Signed and Sealed this
Thirty-first Day of May, 2022

Katherine Kelly Vidal
*Director of the United States Patent and Trademark Office*

CERTIFICATE OF CORRECTION (continued)
U.S. Pat. No. 11,091,427 B2

In the Claims

Column 31, Lines 45-50, Claim 11: Replace Formula IIb with the following:

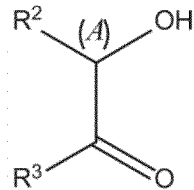

Column 32, Lines 1-7, Claim 14: Replace Formula IIc with the following:

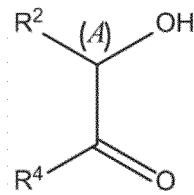

Column 32, Lines 27-32, Claim 16: Replace Formula IId with the following:

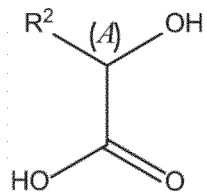

Column 32, Line 37, Claim 16: Delete "$R^4$H.HX" and insert -- $R^4$H·HX --

Column 32, Line 60, Claim 17: Delete "A is 5" and insert -- A is S --

Column 32, Line 61, Claim 17: Delete "A is K" and insert -- A is R --